United States Patent [19]

Brouwer et al.

[11] 3,964,896
[45] June 22, 1976

[54] OXADIAZOLE BENZOIC ACID DERIVATIVES AS HERBICIDES

[75] Inventors: Walter G. Brouwer, Guelph; Edwin J. MacPherson, Elmira, both of Canada; Ronald B. Ames, Naugatuck; Robert W. Neidermyer, Cheshire, both of Conn.

[73] Assignee: Uniroyal, Inc., New York, N.Y.

[22] Filed: Feb. 5, 1975

[21] Appl. No.: 547,155

Related U.S. Application Data

[62] Division of Ser. No. 170,263, Aug. 9, 1971, Pat. No. 3,882,138.

[52] U.S. Cl. .................................. 71/92
[51] Int. Cl.² .............................. A01N 9/22
[58] Field of Search ........................ 71/92

[56] References Cited
UNITED STATES PATENTS

| | | | |
|---|---|---|---|
| 3,128,171 | 4/1964 | Tischler | 71/115 |
| 3,130,205 | 4/1964 | Richter | 71/115 X |
| 3,130,206 | 4/1964 | Richter | 71/115 X |
| 3,808,223 | 4/1974 | Dahle et al. | 71/92 X |

Primary Examiner—Lewis Gotts
Assistant Examiner—Catherine L. Mills
Attorney, Agent, or Firm—James J. Long

[57] ABSTRACT

New 2-(1,3,4-oxadiazole-2-yl) benzoic acids and salts and esters thereof, as well as certain 2-(2-oxazolyl) benzoic acids, salts and esters, having the formula:

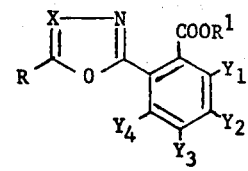

where X is nitrogen or C-R″ (R″ being hydrogen or methyl), R is phenyl or various substituents, and R' and the Y's are hydrogen or various substituents, are effective preemergence or postemergence herbicides, on various crops. The chemicals act selectively and are useful against purple nutsedge and in cranberry. Oxadiazoles of the invention may be made by reacting a benzhydrazide with phthalic anhydride to form a hydrazide which is cyclized by removal of the elements of water, using as a catalyst fuming sulfuric acid or dimethylformamide-sulfur trioxide complex.

6 Claims, No Drawings

OXADIAZOLE BENZOIC ACID DERIVATIVES AS HERBICIDES

This is a division of application Ser. No. 170,263, filed Aug. 9, 1971, now U.S. Pat. No. 3,882,138, issued May 6, 1975.

This invention relates to certain oxadiazoles as new chemicals and methods of making same, and it also relates to the use of such oxadiazoles, and certain oxazoles, as herbicides.

Weeds are undesirable plants because they compete with crops for available space, light, nutrients and moisture, causing reductions in crop yield, because they lower crop quality, harbor diseases and insect pests of plants and adversely affect the usefulness of non-crop land. The cost of controlling weeds has been reduced by the use of herbicides. In accordance with the present invention it has now been found that certain derivatives of 2-(1,3,4-oxadiazole-2-yl) benzoic acid and 2-(2-oxazolyl) benzoic acid, herein referred to as oxadiazoles and oxazoles, respectively, are effective as herbicides.

The oxazoles and oxadiazoles found to be active as herbicides in accordance with the invention are benzoic acids (or salts or esters thereof) having the following structure:

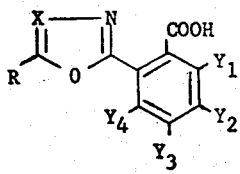

wherein:

X is nitrogen or C-R'' (R'' being hydrogen or methyl);

R is hydrogen, lower alkyl, a heterocyclic group or the group

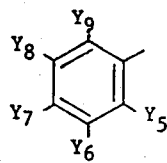

and the Y's are the same or different and are selected from the group consisting of hydrogen, halogen, nitro, lower alkyl, and lower alkoxy.

The chemicals in which X is nitrogen, that is, the 2-(1,3,4-oxadiazole-2-yl) benzoic acids, salts and esters, are believed to be new chemicals.

One preferred sub-class of herbicidal chemicals of the invention is that represented by the formula

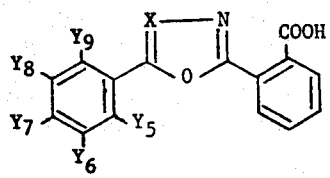

where X and the Y's have the values previously stated. Of these, the new chemicals in which X is nitrogen, that is, the 2-(1,3,4-oxadiazolyl-2-yl) benzoic acids, salts and esters constitute an important sub-class, although the chemicals in which X is CH or C—CH$_3$, that is, the 2-(2-oxazolyl) benzoic acids, salts and esters, are also effective herbicides.

In more detail, herbicidal chemicals of the invention may be represented by the formula

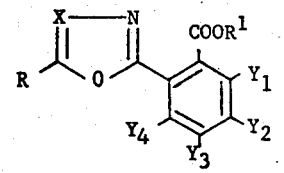

where X, R, and the Y's are as previously defined and R' is hydrogen or a salt-forming or ester-forming moiety. When R' is hydrogen this formula of course represents the benzoic acids themselves. In the salts, R' is typically an alkali metal (preferably sodium or potassium although lithium or other metal may also be used as the salt-forming moiety, including polyvalent metals such as copper, zinc, calcium, barium, magnesium, iron and the like), ammonium, alkylammonium having up to 12 carbon atoms (e.g., methylammonium, ethylammonium, diethylammonium, hexylammonium, dodecylammonium), alkanolammonium having up to 12 carbon atoms (e.g., ethanolammonium, diethanolammonium, hexanolammonium, dodecanolammonium), choline, and the like. In the esters, R' is commonly represented by aliphatic or cycloaliphatic hydrocarbyl moieties having up to 12 carbon atoms, notably alkyl (e.g., methyl, ethyl, n-propyl, iso-propyl, n-butyl, iso-butyl, sec.-butyl, tert.-butyl, hexyl, iso-octyl, dodecyl), alkenyl (e.g., vinyl, allyl, methallyl, 2-hexenyl, 3-hexenyl, 2-dodecenyl, 4-dodecenyl, etc.), alkynyl (e.g., 2-propynyl, 2-butynyl, 3-hexynyl, 3-dodecynyl, etc.), cycloalkyl having up to 12 carbon atoms (e.g., cyclopropyl, cyclohexyl, cyclododecyl, etc.), and the like, or by epoxyalkyl (e.g., 2,3-epoxypropyl, 2,3-epoxybutyl, 3,4-epoxybutyl, 2,3-epoxyhexyl, 4,5-epoxyoctyl, 2,3-epoxydodecyl, 5,6-epoxydodecyl, etc.) In addition to the acids themselves (R' is hydrogen) preferred bodies are the alkali metal salts (R' is alkali metal) and the alkyl esters (R' is alkyl).

In other preferred chemicals the benzoic acid ring is unsubstituted (that is, Y$_1$, Y$_2$, Y$_3$, and Y$_4$, are hydrogen).

Also particularly advantageous in certain respects are chemicals in which the 5-substituent (R) on the oxazole or oxadiazole ring is phenyl, that is, Y$_5$, Y$_6$, Y$_7$, Y$_8$ and Y$_9$ are all hydrogen, or a mono-substituted phenyl, that is, all but one of Y$_5$, Y$_6$, Y$_7$, Y$_8$ and Y$_9$ are hydrogen (although di-, tri-, tetra- and penta- substituted phenyl bodies as defined herein may also be used).

Examples of oxadiazoles and oxazoles useful in the control of weeds in accordance with the invention are 2-(5-phenyl-1,3,4-oxadiazole-2-yl) benzoic acid, the methyl ester of same, the ethyl ester of same, the butyl ester of same, the n-hexyl ester of same, the n-dodecyl ester of same (or similar alkyl esters in which the alkyl group is normal or iso, primary, secondary or tertiary, straight chain or branched), 2-[5-(2-tolyl)-1,3,4-oxadiazole-2-yl] benzoic acid (also the 3-tolyl and 4- tolyl analogs of same), ethyl 2-[5-(2,3-dimethylphenyl)-1,3,4-oxadiazole-2-yl] benzoate, 2-(5-methyl-1,3,4-oxadiazole-2-yl) benzoic acid, sec.-butyl 2-(5-n-hexyl-1,3,4-oxadiazole-2-yl) benzoate, 2-(5-isopropyl-1,3,4-oxadiazole-2-yl) benzoic acid, amyl 2-[5-(2,3,4-trimethylphenyl)-1,3,4-oxadiazole-2-yl) benzoate, 2-[5-(4-chlorophenyl)-1,3,4-oxadiazole-2-yl] benzoic acid, methyl 2-[5-(2,3,4-tribromophenyl)-1,3,4-oxadiazole-2-yl] benzoate, 2-[5-(3-nitrophenyl)-1,3,4-oxadiazole-2-yl] benzoic acid, isopropyl 2-[5-(2-chloro-3-nitro-4-methoxyphenyl)-1,3,4-oxadiazole-2-yl] benzoate, methyl 2-[5-(2,3,4-trimethoxyphenyl)-1,3,4-oxadiazole-2-yl] benzoate, ethyl 2-(5-ethyl-1,3,4-oxadiazole-2-yl) benzoate, tert.-butyl 2-(5-phenyl-2-oxazolyl) benzoate, methyl 2-[5-(2-fluoro-3-anisyl)-4-methyl-2-oxazolyl] benzoate, 2-[5-(2-nitrophenyl)-2-oxazolyl] benzoic acid, 2-[5-(2,3,4-trichlorophenyl)-2-oxazolyl] benzoic acid, sodium 2-[5-(2,3,4-trichlorophenyl)-2-oxazolyl] benzoate, n-dodecyl 2-[4-methyl-5-(3-pyridyl)-2-oxazolyl] benzoate, ethyl 2-[5-(2,3,4,5-tetrachlorophenyl)-1,3,4-oxadiazole-2-yl] benzoate, ethyl 2-[5-(2,3,4,5,6-pentachlorophenyl)-1,3,4-oxadiazole-2-yl] benzoate, 2-[5-(2,3-dibromo-4-butoxy-5-nitrophenyl)-4-methyl-2-oxazolyl]-3-ethylbenzoic acid, isobutyl 2-[5-phenyl-1,3,4-oxadiazole-2-yl]-3,4,5-trichlorobenzoate, methyl 2-[4-methyl-5-(2-anisyl)-2-oxazolyl]-3-bromo-6-nitrobenzoate, dodecyl 2-[4-methyl-5-phenyl-2-oxazolyl]-tetrachloro benzoate, potassium 2-(5-phenyl-2-oxazolyl) benzoate, ammonium 2-[5-phenyl-1,3,4-oxadiazole-2-yl] benzoate, diethanolammonium 2-[5-(2-n-butylphenyl)-1,3,4-oxadiazole-2-yl]-4-fluorobenzoate, 2-[5-(5-chloro-3-pyridyl)-1,3,4-oxadiazole-2-yl] benzoic acid, cyclohexyl 2-(5-phenyl-1,3,4-oxadiazole-2-yl) benzoate, n-butyl 2-(5-phenyl-2-oxazolyl) benzoate, allyl 2-[5-(4-nitrophenyl(-1,3,4-oxadiazole-2-yl]-5-methyl benzoate, vinyl 2-(5-phenyl-2-oxazolyl) benzoate, methallyl 2-(4-methyl-5-phenyl-2-oxazolyl) benzoate, 5-pentenyl 2-(5-phenyl-1,3,4-oxadiazole-2-yl) benzoate, 2-hexenyl 2-[5-(3-ethylphenyl)-1,3,4-oxadiazole-2-yl] benzoate, 3-butynyl 2-(5-phenyl-2-oxazolyl)-4-methoxy benzoate, 3-hexynyl 2-(4-methyl-5-phenyl-2-oxazolyl) benzoate, 2-pentynyl 2-[5-(2-chlorophenyl)-1,3,4-oxadiazole-2-yl] benzoate, cyclopentyl 2-(5-phenyl-1,3,4-oxadiazole-2-yl) benzoate, cyclooctyl 2-(4-methyl-5-phenyl-2-oxazolyl) benzoate, 2,3-epoxypropyl 2-(5-phenyl-1,3,4-oxadiazole-2-yl) benzoate, ferric tri[2-(5-phenyl-1,3,4-oxadiazole-2-yl) benzoate], manganese di[2-(5-phenyl-2-oxazolyl) benzoate], 5-iodo-2-(5-phenyl-1,3,4-oxadiazole-2yl) benzoic acid, 3,5-diiodo-2-(5-phenyl-1,3,4-oxadiazole-2-yl) benzoic acid, 6-nitro-2-(5-phenyl-1,3,4-oxadiazole-2-yl) benzoic acid, 2-(5-phenyl-1,3,4-oxadiazole-2-yl)-3,5,6-trimethoxy benzoic acid, 3-chloro-2-(5-phenyl-1,3,4-oxadiazole-2-yl) benzoic acid, 2-(5-phenyl-1,3,4-oxadiazole-2-yl)-3,5,6-trimethyl benzoic acid, 2-(5-phenyl-1,3,4,-oxadiazole-2-yl)-3,4,5,6-tetrachloro benzoic acid, 2-(5-phenyl-1,3,4-oxadiazole-2-yl)-3,4,5,6-tetrabromobenzoic acid, 2-[5-(2-chloro-3,5-dinitrophenyl)-1,3,4-oxadiazole-2-yl] benzoic acid, 2-[5-(2,4-dichloro-3,5-dinitrophenyl)-1,3,4-oxadiazole-2-yl] benzoic acid, 2-[5-(2,4- dichloro-3,5-dinitrophenyl)-1,3,4-oxadiazole-2-yl] benzoic acid, 2-[5-(2-methyl-3,5-dinitrophenyl)-1,3,4-oxadiazole-2-yl] benzoic acid, 2-[5-(3,4,5-trimethoxyphenyl)--methyl-3,51,3,4-oxadiazole-2-yl] benzoic acid, 2-[5-(2-methyl-4-nitrophenyl)-1,3,4-oxadiazole-2-yl] benzoic acid, 2-[5-(2-methyl-4-nitrophenyl)-1,3,4-oxadiazole-2-yl] benzoic acid, 2-[5-(2-methyl-5-nitrophenyl)-1,3,4-oxadiazole-2-yl] benzoic acid, 2-(1,3,4-oxadiazole-2-yl) benzoic acid, N-butyl 2-(1,3,4-oxadiazole-2-yl) benzoate, 2-[5-(2,4,5-trimethyl-3-furyl)-1,3,4-oxadiazole-2-yl] benzoic acid, 2-[5-(2-furyl)-1,3,4-oxadiazole-2-yl] benzoic acid, 2-[5-(2,5-dimethyl-3-furyl)-1,3,4-oxadiazole-2-yl] benzoic acid, 2-[5-(2-methyl-3-furyl)-1,3,4-oxadiazole-2-yl] benzoic acid, 2-[5-(3-furyl)- 1,3,4-oxadiazole-2-yl] benzoic acid, 2-[5-(4-methyl-2-[3-pyridyl]-5-thiazolyl)-1,3,4,-oxadiazole-2-yl] benzoic acid, 2 -[5-(4-pyridyl)-1,3,4-oxadiazole-2-yl] benzoic acid, 2-[5-(2-pyridyl)-1,3,4-oxadiazole-2-yl] benzoic acid, 2-[5-(3-pyridyl)-1,3,4-oxadiazole-2-yl] benzoic acid, and the like.

It is desired to emphasize that the herbicidal chemicals employed herein are mono benzoic acid types. Also, a necessary requirement for activity is the ortho carboxylic acid or carboxylate group.

As indicated, the invention is also concerned with novel methods of making certain new 2-(1,3,4-oxadiazole-2-yl) benzoic acid chemicals. One such new method, herein below refered to as Method Ia, involves the preparation of 2-(1,3,4-oxadiazole-2-yl) benzoic acids of the formula

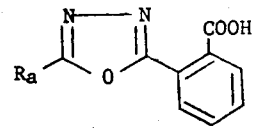

wherein $R_a$ is selected from the group consisting of phenyl, 2-chlorophenyl, 4-chlorophenyl, 2-methylphenyl, 3-methylphenyl and 4-methylphenyl. According to this method, a hydrazide of the formula

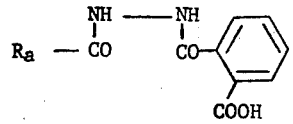

(wherein $R_a$ is as previously defined) is mixed with sulfur trioxide in dimethylformamide medium at a temperature of from —10° to 20°, and thereafter the 2-(1,3,4-oxadiazole-2-yl) benzoic acid of the stated formula is recovered from the mixture. In the course of the reaction the elements of water are removed from the precursor. In this method the selection of the starting hydrazide chemical is critical, since otherwise similar chemicals, in which the value of $R_a$ is other than the values above stated, are inoperative. Also critical is the use of sulfur trioxide-dimethylformamide complex as the cyclizing agent, since numerous other common cyclizing agents are inoperative. Thus, such cyclizing agents as phosphorus oxychloride, thionyl chloride, polyphosphoric acid, etc., fail to accomplish cyclization. Also critical is the temperature at which the reaction is carried out, since at higher temperatures than those stated, very poor yields are obtained. The proportions of hydrazide starting chemical, sulfur trioxide and dimethylformamide are not critical and may vary widely. For example, for each mole of hydrazide starting chemical employed, there may be used from 1 mole to 3 moles or more of sulfur trioxide and from 10 moles to 15 moles or more of dimethylformamide.

In accordance with another method of the invention, hereinbelow referred to as Method Ic, the new chemical 2-(1,3,4-oxadiazole-2-yl) benzoic acid itself, is prepared according to a similar procedure, but employing fuming sulfuric acid as the agent to remove the elements of water and bring about cyclization. In this novel method the hydrazide chemical, namely, 1-benzoyl-2-(2-carboxybenzoyl) hydrazine

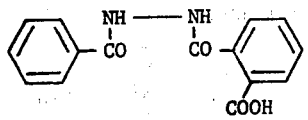

is mixed with fuming sulfuric acid at a temperature of from −10° to 20°, and thereafter the 2-(1,3,4-oxadiazolyl-2-yl) benzoic acid

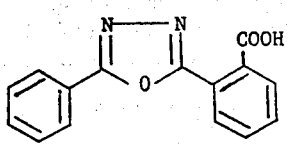

is recovered from the mixture. Cooling is necessary to maintain the temperature within the stated range during the cyclodehydration. In this method the selection of the specific cyclizing agent, fuming sulfuric acid, is critical, as is the use of relatively low reaction temperature. The proportions of the starting hydrazide chemical and fuming sulfuric acid are not critical and may vary widely. For example, for each 100 parts by weight of starting hydrazide there may be employed from 200 parts to 800 parts by weight or more of fuming sulfuric acid (or 100 parts to 400 parts by volume). The concentration of sulfur trioxide in the fuming sulfuric acid is conventional and usually ranges from 15 to 30% by weight.

It will be noted that in the foregoing methods the carboxylic acid group is present throughout. Other methods useful for making chemicals employed in the invention, to be described below, include syntheses which involve a group such as methyl, chloromethyl, dichloromethyl, trichloromethyl, formyl, acetyl, ester, etc., which can be chemically converted to the carboxylic acid group when required.

The following are the methods of synthesis:

Method Ia

Formula description:

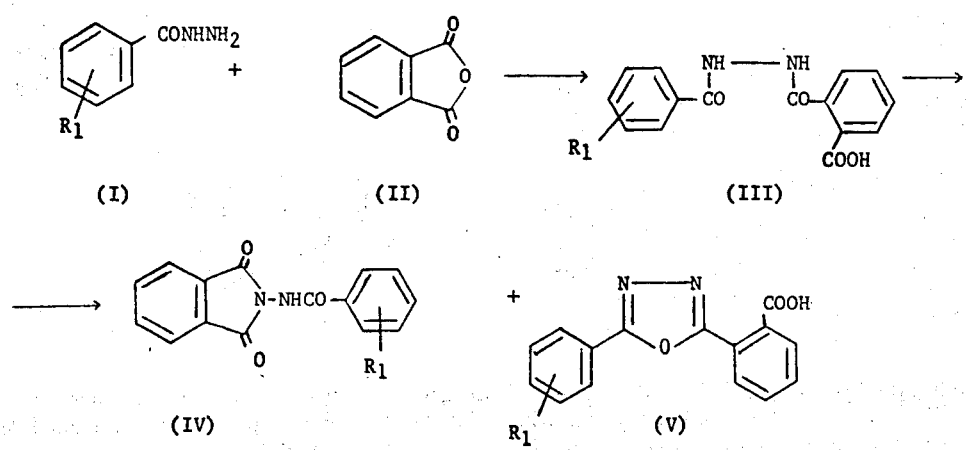

A derivative of benzhydrazide (I) is heated with phthalic anhydride (II) in an inert solvent to give a quantitative yield of the hydrazide (III) where $R_1$ is hydrogen or certain substituents. This hydrazide (III) can be cyclized by dimethylformamide-sulphur trioxide complex to two products, a phthalimido derivative (IV) or a 2-(1,3,4-oxadiazole-2-yl) benzoic acid (V). The respective yields of these two products vary depending upon the $R_1$ substituent. In some cases the yield of the 1,3,4-oxadiazole (i.e. compound V) is zero. Pyrolysis of 2-(1,3,4-oxadiazole-2-yl) benzoic acids results in the formation of the phthalimido derivative (i.e. IV). The phthalimido derivative (IV) can be converted to hydrazide (III) on treatment with aqueous base followed by neutralization with aqueous acid, and the hydrazide (III) can be recyclized to (IV) and (V). The invention, in its first method aspect, is based on the discovery that when $R_1$ is hydrogen (preferred) or is a substituent selected from 2-chloro, 4-chloro, 2-methyl, 3-methyl or 4-methyl, the specific cyclizing agent (dimethylformamide-sulfur trioxide complex) unexpectedly produces the desired product (V), as indicated previously.

Method Ib

Formula description:

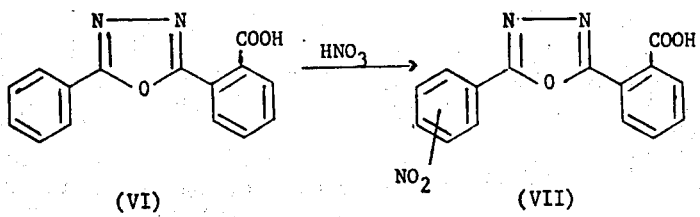

This method involves the nitration of 2-(5-phenyl-1,3,4-oxadiazole-2-yl) benzoic acid (VI) which was prepared by Method Ia. Nitration occurs exclusively in the 5-phenyl ring. The nitro derivatives produced can be separated by crystallization.

Method Ic

This method of the invention is similar to that of Method Ia except that fuming sulfuric acid is used to cyclize the hydrazide (III) [specifically, $R_1$ is hydrogen, i.e. 1-(2-carboxybenzoyl)-2-benzoylhydrazine] to 2-(5-phenyl-1,3,4-oxadiazole-2-yl) benzoic acid.

Method Id

This method involves synthesis of esters. A 2-(1,3,4-oxadiazole-2-yl) benzoic acid derivative in chloroform in the presence of an excess of thionyl chloride is refluxed till the evolution of hydrogen chloride and sulfur dioxide ceases. After the removal of chloroform and excess thionyl chloride the residue (the acid chloride of the oxadiazole acid) is dissolved in toluene or benzene and added to a solution of appropriate alcohol in toluene or benzene along with an organic base to act as hydrogen chloride acceptor. The mixture is washed with water, dilute acid, dilute bicarbonate, dried and the solvent removed. The esters so produced are usually viscous oils.

Esterification can also be brought about by diazotization or by the reaction of the sodium or potassium salt of an oxadiazole acid with an alkyl halide.

Method II

Formula description:

zine (IX) which can be cyclized to a 2-aryl-5-o-tolyl-1,3,4-oxadiazole (X) by any of the standard cyclizing agents reported in the literature. The methyl group ($CH_3$) on the diphenyloxadiazole (X) can be converted by permanganate oxidation to a 2-(5-phenyl-1,3,4-oxadiazole-2-yl) benzoic acid (V).

Method IIIa

Formula description:

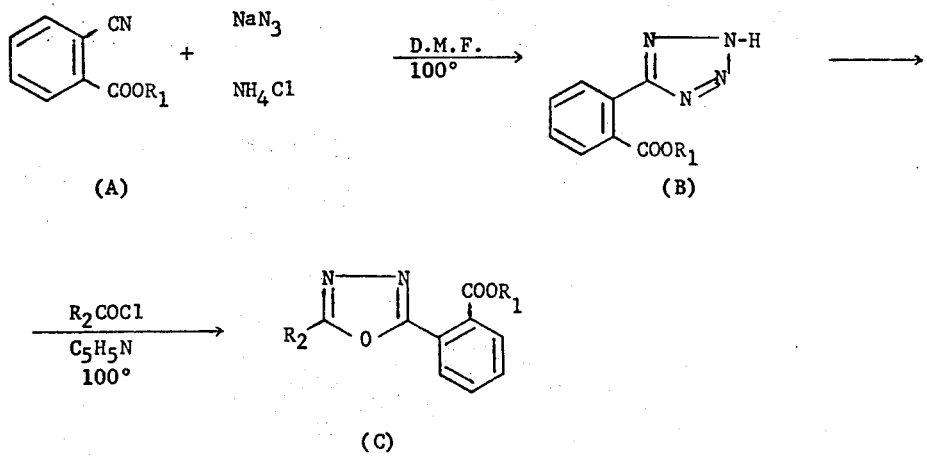

In this method a 2-cyanobenzoic acid or ester (A) can be converted to a tetrazolyl derivative (B) by heating with excess sodium azide/ammonium chloride in dimethylformamide (D.M.F.). When this tetrazole is treated with an acid chloride in pyridine and subsequently heated, it rearranges with the loss of hydrogen chloride and nitrogen to the oxadiazole (C). The method is especially appropriate for preparation of products in which the benzoic acid nucleus is variously substituted, although it is also applicable to products having no substituents on the benzoic acid nucleus.

Method IIIb

This method involves the hydrolysis of esters to their corresponding acids. The ester is hydrolyzed in methanolic sodium hydroxide at room temperature. The hydrolysis is usually complete in 2 hours. Room temperature reaction conditions avoid difficulty from decomposition of 2-(1,3,4-oxadiazole-2-yl) benzoic acids or benzoates at elevated temperature.

Method IV

This method involves the chlorination of 2-(5-phenyl-1,3,4-oxadiazole-2-yl) benzoic acid (VI) to 2-(5-chlorophenyl-1,3,4-oxadiazole-2-yl) benzoic acid.

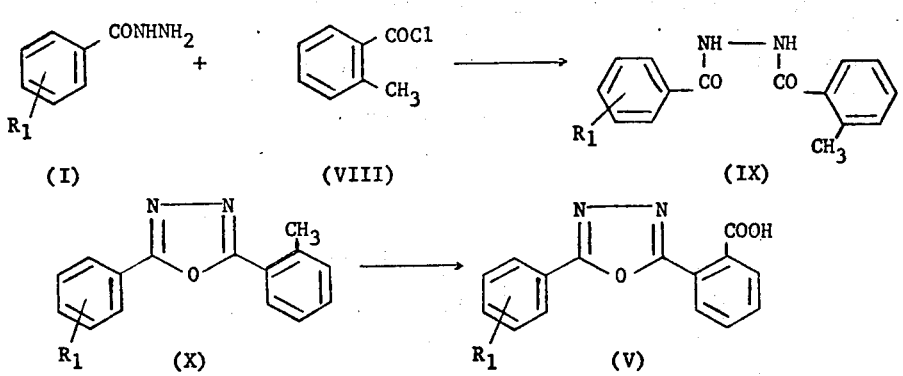

Benzhydrazide derivative (I) is reacted with o-toluoyl chloride (VIII) to produce 1-aroyl-2-o-toluoyl hydra-

Method Va

This method describes the oxazole synthesis.

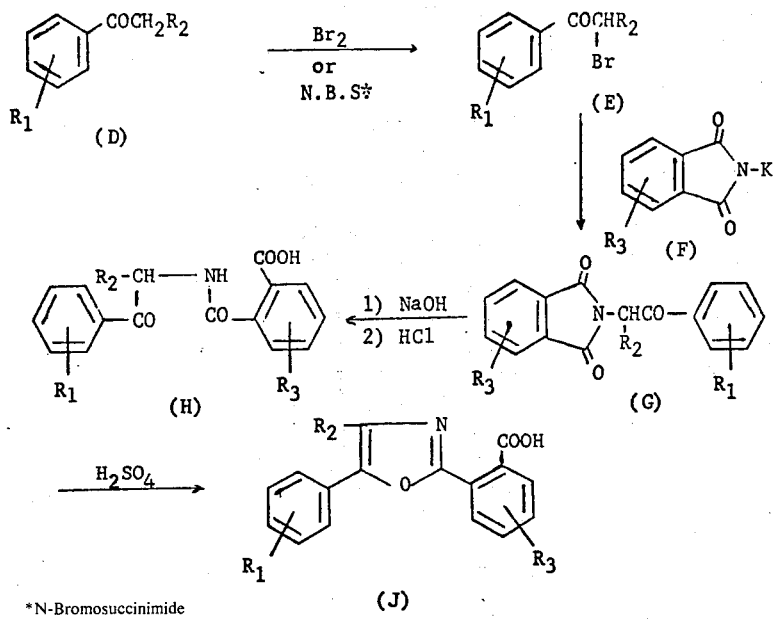

*N-Bromosuccinimide

An acetophenone (D) is brominated to the corresponding bromide (E) which in D.M.F. is treated with an analog of potassium phthalimide (F) to give the corresponding phthalimide (G). Subsequent ring opening with dilute base followed by acidification affords a phthalamic acid (H). Ring closure with concentrated sulfuric acid at room temperature will give a 2-(2-oxazolyl) benzoic acid (J).

Method Vb

The synthesis of the esters of oxazole herbicides may follow standard literature procedure for aromatic ester preparation. The oxazole acid may be refluxed in an excess of appropriate alcohol in the presence of an acid catalyst.

Turning now to the use of the chemicals herein described as herbicides, the method of formulating and using the herbicidal compositions may follow conventional practice and in general involves controlling weeds by applying to a locus containing weed seeds or supporting weed growth a herbicidally effective amount of the chemical.

The herbicides of the invention may be applied before or after crop and/or weed emergence. The chemicals may be applied to the soil or plants in various forms as described below. The chemicals may be impregnated on finely-divided or granular inorganic or organic carriers such as attapulgite clay, sand, vermiculite, corn cobs, activated carbon and other granular carriers known to the art. The impregnated granules may then be spread on the soil. A wettable powder can be prepared by grinding the chemical to a fine powder and mixing it with an inactive powdered carrier to which a surface active dispersing agent has been added. The wettable powder may then be dispersed in water and sprayed on the soil or plants. An emulsifiable concentrate may be prepared by dissolving the chemicals in a solvent such as acetone, benzene, toluene, ethanol, or other aliphatic or aromatic hydrocarbons to which a surface active dispersing agent has been added. The emulsifiable concentrate may then be dispersed in water and sprayed on the soil or plants. Solutions of the chemicals (not the esters) can be prepared by dissolving the chemicals in a stoichiometric amount of an appropriate base such as potassium hydroxide, ammonium hydroxide, sodium hydroxide, or diethanolamine.

The salts formed by such a process are then soluble in water and with the addition of a surface active wetting agent may be sprayed on the soil or plants. Surface active agents as described above are well known to those skilled in the art and reference is made to McCutcheon's Detergents and Emulsifiers, 1970, Allured Publishing Corp., Ridgewood, N.J.; also Hoffman et al. U.S. Pat. No. 2,614,916, columns 2 to 4 or U.S. Pat. No. 2,547,724, columns 3 and 4.

Two specific advantages of the present compounds as herbicides are:

1. Control of Cyperaceae spp. Currently there are few selective herbicides for the control of these species. Purple nutsedge (*Cyperus rotundus* L.) is said to be the world's worst weed.

2. Efficacy as a selective herbicide in cranberry. There are few herbicides for this use.

The following examples, in which all quantities are expressed by weight unless otherwise indicated, will serve to illustrate the practice of the invention in more detail.

EXAMPLE 1. Method Ia

Step 1. 1-Benzoyl-2-(2-carboxybenzoyl) hydrazine

At a temperature of about 18°, powdered benzhydrazide (126 g, 1 mole) was suspended in stirred benzene (1.6 l), and 24-mesh phthalic anhydride (148 g, 1 mole) was added portionwise over 15 to 20 minutes. After the addition the reaction mixture was stirred for a further hour. The product, 1-benzoyl-2-(2-carboxybenzoyl) hydrazine (III) ($R_1$=H) was collected on a filter, pressed free of benzene and air dried, 276 g, 98%, M.P., 205°–208°.

Step 2. 2-(5-Phenyl-1,3,4-oxadiazole-2-yl) benzoic acid.

Dry dimethylformamide (D.M.F.) (300 ml) was cooled in an ice-bath and with stirring treated dropwise with sulphur trioxide ($SO_3$) (100 ml) such that the temperature did not exceed 5°. With continued ice-bath cooling the D.M.F./$SO_3$ complex was treated dropwise with a solution of 1-benzoyl-2-(2-carboxybenzoyl)-hydrazine (148.5 g, 0.52 mole) dissolved in dry D.M.F. (200 ml). After the addition, the reaction was stirred for a further ½ hour at 0° and then for several hours with the ice-bath removed. The reaction mixture was poured into water (2 l) and allowed to stand until the paste which separated became hard. The crude product was collected on a filter, washed well with water, then air dried, wt. 143 g. This crude product was stirred into a solution of sodium bicarbonate (150 g) in water (1.4 l) till all effervescence had ceased. Undissolved material was collected on a filter, washed with water and air dried, 26 g (18%). Recrystallization from methanol gave white crystals of N-phthalimidobenzamide, (IV) ($R_1$=H), M.P. 215°–218°.

Acidification of the bicarbonate extract gave a precipitate which was collected on a filter, washed with water and air dried, 116 g (82%). A portion was recrystallized from acetone to give 2-(5-phenyl-1,3,4-oxadiazole-2-yl)-benzoic acid (V) ($R_1$=H), M.P. 172.6°. Analysis gave C, 67.55; H, 3.75; N, 10.26. $C_{15}H_{10}N_2O_3$ requires C, 67.66; H, 3.79; N, 10.52.

Step 3. Conversion of N-phthalimidobenzamide to 1-benzoyl-2-(2-carboxybenzoyl)-hydrazine N-Phthalimidobenzamide (353 g, 1.32 mole) was dissolved in a slight excess of 2N sodium hydroxide solution. After filtering, the reaction mixture was poured into 2N hydrochloric acid. The precipitate, 1-benzoyl-2-(2-carboxybenzoyl)hydrazine was filtered, washed with water and air dried, wt. 368 g.

EXAMPLE 2. Method II

Step 1. 1-(2-Chlorobenzoyl)-2-(2-toluoyl)-hydrazine o-Chlorobenzhydrazide (80 g, 0.47 mole) was suspended in benzene (1 l) to which was added pyridine (38.2 ml). With vigorous stirring, the suspension was treated dropwise with o-toluoyl chloride (74.5 g, 0.48 mole) and on completion the reaction was heated to reflux over 2 hours. After cooling, the product was filtered and washed with water. Recrystallization from 75% ethanol gave 1-(2-chlorobenzoyl)-2-toluoyl)-hydrazine (IX) ($R_1$=o-Cl) 107.5 g, 79%, M.P. 206°–208°. (Found: C, 62.94; 62.97; H, 4.73, 4.74; N, 9.57, 9.54. $C_{15}H_{13}ClN_2O_2$ requires C, 62.39; H, 4.54; N, 9.90).

Step 2. 2-(2-Chlorophenyl)-5-(2-tolyl)-1,3,4-oxadiazole

Dry D.M.F. (160 ml) was cooled in an ice bath and with stirring treated dropwise with $SO_3$ (55 ml) such that the temperature did not exceed 5°. On completion the D.M.F.-$SO_3$ complex was treated with a solution of 1-(2-chlorobenzoyl)-2-(2-toluoyl)-hydrazine (IX) ($R_1$=o-Cl) (87.5 g, 0.3 mole) dissolved in dry D.M.F. (170 ml). The reaction mixture was stirred in the ice-bath for 1½ hours, then heated on the steam bath till it was homogenous. The reaction mixture was poured into ice-water and the solid which precipitated was collected on a filter, washed with water and air dried. Recrystallization from ethanol gave 2-(2-chlorophenyl)-5-(2-tolyl)-1,3,4-oxadiazole (X) ($R_1$=o-Cl), 48.5 g, 59%, M.P. 102°–4°. Found, C, 65.96, 65.92; H, 4.10, 4.05; N, 10.07, 10.00. $C_{15}H_{11}ClN_2O$ requires C, 66.55; H, 4.10; N, 10.35.

Step 3. 2-[5-(2-Chlorophenyl)-1,3,4-oxadiazole-2-yl] benzoic acid 2-(2-Chlorophenyl)-5-(2-tolyl)-1,3,4-oxadiazole (X) ($R_1$=o-Cl) (27 g, 0.1 mole) was added to a stirred solution of potassium permanganate (38 g, 0.24 mole) in water (500 ml). The mixture was heated to reflux. Refluxing was continued till the color of the permanganate had discharged. The reaction mixture was filtered hot and the manganese dioxide on the filter was washed with hot water (100 ml), then extracted with cold acetone. Removal of the acetone yielded starting material (13 g after recrystallization).

The combined aqueous filtrate was acidified, extracted with ether and the ether extract washed with water and dried. Evaporation of the ether left an oil which slowly solidified, 1.5 g, 9.6% (based on amount of (X) ($R_1$=o-Cl) consumed). Recrystallization from acetone gave 2-[5-(2-chlorophenyl)-1,3,4-oxadiazole-2-yl] benzoic acid (V) ($R_1$=o-Cl), M.P. 142°–4°. (Found, C, 59.77 59.68; H, 3.28, 3.10; N, 9.17, 8.84. $C_{15}H_9ClN_2O_3$ requires C, 59.91; H, 3.02; N, 9.32.)

EXAMPLE 3. Method Ib

2-[5-(2-Nitrophenyl)-1,3,4-oxadiazole-2-yl]-benzoic acid and
2-[5-(3-nitrophenyl)-1,3,4-oxadiazole-2-yl]benzoic acid.

Finely-powdered 2-(5-phenyl-1,3,4-oxadiazole-2-yl) benzoic acid (VI) (133 g, 0.5 mole) was added portionwise to stirred concentrated sulphuric acid (200 ml) kept cool in an ice-bath. On completion, the mixture was treated drop-wise while stirring with a solution of concentrated sulphuric acid (42 ml) in nitric acid (42 ml, S.G. 1.42) such that the temperature did not exceed 5°. After the addition, the reaction mixture was stirred for a further 2 hours in the ice-bath and then poured into cold water (4 l). The yellow solid which precipitated was filtered, washed well with water, and the air dried, 143 g.

A 10 g portion of crude product was stirred in cold methanol (100 ml) for 1½ hours. Undissolved material was collected and dried, 6.5 g. The mother liquor was concentrated to 50 ml to give a second crop of 1 g. Two types of crystals separated when the mother liquor was concentrated to 25 ml. The amber-coloured crystals were hand picked to yield 0.8 g of material which was recrystallized from methanol to give 2-[5-(2-nitrophenyl)-1,3,4-oxadiazole-2-yl] benzoic acid (VII) ($R_1$=o-$NO_2$), M.P. 182°–7°. Yield estimated at about 10–15%. (Found: C, 57.96, 57.42; H, 2.97, 3.07; N, 13.51, 13.52. $C_{15}H_9N_3O_5$ requires C, 57.88; H, 2.91; N, 13.50.)

The remaining light yellow crystals were combined with the other two crops and recrystallized from acetone to give 2-[5-(3-nitrophenyl)-1,3,4-oxadiazole-2-yl] benzoic acid (VII) ($R_1$=(m-$NO_2$), M.P. 222°–6°. Yield estimated at 85–90%. (Found: C, 57.94, 58.06; H, 2.96, 3.00; N, 13.64, 13.49. $C_{15}H_9N_3O_5$ requires C, 57.88; H, 2.91; N, 13.50.)

EXAMPLE 4. Method Ic

2-(5-Phenyl-1,3,4-oxadiazole-2-yl) benzoic acid

Fuming sulphuric acid (100 ml) (20%) was cooled in an ice/salt bath, then with vigorous stirring treated portionwise with powdered 1-(2-carboxybenzoyl)-2-benzoylhydrazine (113.6 g, 0.4 mole) such that the temperature did not exceed 0° (time of addition, 15-20 mins.). On completion of the addition, the reaction mixture was stirred for a further ¾ hour, then poured into ice water. The precipitated solid was filtered, washed with water and digested with aqueous sodium bicarbonate. The undissolved material was collected, washed with water and dried, to give N-phthalimidobenzamide, M.P. 210°–4°, 13 g.

Acidification of the aq. bicarbonate solution gave 2-(5-phenyl-1,3,4-oxadiazole-2-yl) benzoic acid, which was filtered, washed with water and dried, M.P. 163°–170°, 84 g, 79%.

EXAMPLE 5. Method IIIa

Step 1. Phthalamic acid

With vigorous stirring, concentrated ammonia solution (900 ml, S.G. 0.9) was treated portionwise with phthalic anhydride (600 g, 4.0 moles) over a period of 1½ hrs. After the reaction mixture had cooled to room temperature, the precipitated ammonium phthalamate was filtered, then dissolved in the minimum of water. When this solution was acidified to pH 2, phthalamic acid began to crystalize, M.P. 132°-6°.

Acidification of the ammoniacal mother liquor gave a 2nd crop. Total weight of product, 551 g, 78%.

Step 2. Methyl 2-cyanobenzoate

Phthalamic acid (240 g, 1.37 moles) in methylenechloride (1.7 l) was stirred and cooled to <5° in an ice bath. Triethylamine (244 ml, 176 g, 1.74 moles) was added and a clear solution was obtained. Methyl chloroformate (200 g, 163 ml, 2.1 moles) was added at such a rate that the temperature did not exceed 5°. As the addition continued, triethylamine hydrochloride precipitated and carbon dioxide was evolved. On completion of the addition, the ice bath was removed and stirring was continued for 12–20 hrs. at room temperature. Triethylamine hydrochloride was removed by filtration and the methylene chloride evaporated. The residue was dissolved in ether (2 l), and this ether solution washed with water, dried over anhydrous sodium sulfate and evaporated. Distillation under reduced pressure gave methyl 2-cyanobenzoate, b.p. 125° at 2.5 mm, 215 g (97%), a solid at room temperature, M.P. 45°–6°.

Step 3. Methyl 2-(5-2H-tetrazolyl)benzoate

Methyl 2-cyanobenzoate (54 g, 0.33 mole) in D.M.F. (165 ml) was treated with sodium azide (23.4 g, 0.36 mole) and ammonium chloride (19.3 g, 0.36 mole). After the reaction mixture had been stirred on the steam bath for 20 hrs., the D.M.F. was removed under reduced pressure and the residue dissolved in water (200 ml). The solution was filtered, cooled in ice and acidified to give a white precipitate which was filtered, washed with water and dried. This gave methyl 2-(5-2H-tetrazolyl)benzoate, M.P. 132°–5°, 19 g (28%). (Found: C, 53.79, 52.59, 52.33; H, 4.25, 4.17, 4.07; N, 26.79, 26.84, 27.25. $C_9H_8N_4O_2$ requires C, 52.94; H, 3.95; N, 27.44.)

Step 4. Methyl 2-[5-(4-nitrophenyl)-1,3,4-oxadiazole-2-yl]benzoate

Methyl 2-(5-2H-tetrazolyl)benzoate (2 g, 0.01 mole) in pyridine (30 ml) was treated with p-nitrobenzoyl chloride (3.6 g, 0.02 mole). Heat was emitted and a white precipitate appeared. Heating on the steam bath produced a homogeneous reaction mixture and effervescence occurred. After ½ hour, gassing ceased, the reaction mixture was cooled, treated with a few drops of water and allowed to stand for 15 mins. Addition of water (500 ml) gave a light yellow precipitate which was collected, washed with water and dried. Recrystallization from acetone gave yellow crystals of methyl 2-[5-(4-nitrophenyl)-1,3,4-oxadiazole-2-yl] benzoate, M.P. 170°–2°, 2.2 g, 70%. (Found: C, 59.08; H, 3.50; N, 12.76. $C_{16}H_{11}N_3O_5$ requires C, 59.08, H, 3.41; N, 12.92.)

EXAMPLE 6. Method V

Step 1. N-alpha-Methylphenacylphthalimide

To a stirred solution of 2-bromopropiophenone (21.3 g, 0.1 mole) in D.M.F. (80 ml) was added portionwise over 10 mins. potassium phthalimide (20 g, 0.12 mole). The temperature rose slightly and after stirring for 3 hours the reaction mixture was poured into water (600 ml). The yellow precipitate was collected, washed with water and dried. Recrystallization from ethanol gave N-alpha-methylphenacylphthalimide, M.P. 82°–4°, 21.5 g, (77%).

Step 2. N-alpha-Methylphenacylphthalamic acid

N-alpha-Methylphenacylphthalimide (27.9 g, 0.1 mole) was added to 1 N sodium hydroxide (110 ml) and stirred for 24 hrs. The resulting solution was filtered and poured into stirred N/2 hydrochloric acid (240 ml). N-alpha-Methylphenacylphthalamic acid was collected, washed with water and dried, M.P. 132°–6°, 20.3 g, (68%).

Step 3. 2-(4-Methyl-5-phenyl-2-oxazolyl) benzoic acid

N-alpha-Methylphenacylphthalamic acid (20.3 g, 0.068 mole) was added portionwise to conc. sulphuric acid (50 ml) over 15 mins. during which time the temperature rose to 40°. The reaction mixture was stirred for 24 hrs. then poured into ice water (500 ml). The resulting precipitate was filtered, washed with water and digested with aqueous sodium bicarbonate. Acidification of the aqueous bicarbonate solution and crystallization from water/ethanol (1:1) gave 2-(4-methyl-5-phenyl-2-oxazolyl) benzoic acid, M.P. 188°–190°, 12 g, (63%). (Found: C, 72.07, 72.11; H, 4.83, 4.77; N, 4.99, 4.98. $C_{17}H_{13}NO_3$ requires C, 73.3; H, 4.66; N, 4.06.)

EXAMPLE 7. Method IIIb

2-(5-Phenyl-1,3,5-oxadiazole-2-yl) benzoic acid

Benzoyl chloride (2.8 g, 0.2 mole) was added dropwise to a solution of methyl 2-(5-2H-tetrazolyl) benzoate (2 g, 0.01 mole) in pyridine (30 ml). Heat was emitted and a precipitate of pyridine hydrochloride appeared. Heating on the steam bath caused the evolution of nitrogen. After ½ hour, all effervescence had ceased, the reaction mixture was cooled, a few drops of water added and the reaction allowed to stand 15 mins. An oil was obtained when the reaction mixture was added to cold water (500 ml). This oil was dissolved in ether. The ether extract was washed with dilute acid, dilute bicarbonate solution and water then dried over anhydrous sodium sulphate and evaporated.

The crude oil so obtained was dissolved in methanol (20 ml) and added to a solution of sodium hydroxide (0.5 g) in methanol (20 ml). After this solution had been stirred at room temperature for 1 hour, the methanol was removed, the residue dissolved in water, washed with ether and acidified. The solid which precipitated was filtered, washed with water and dried. 1.5 g (56%) of crude product was obtained. Recrystallization from ethanol gave 2-(5-phenyl-1,3,4-oxadiazole-2-yl) benzoic acid, M.P. 175°–7°. The infrared spectrum was identical to that of 2-(5-phenyl-1,3,4-oxadiazole-2-yl) benzoic acid made by methods Ia, Ic and II.

EXAMPLE 8. Method II 2-(5-Phenyl-1,3,4-oxadiazole-2-yl) benzoic acid

2-Phenyl-5-(2-tolyl)-1,3,4-oxadiazole (47.2 g, 0.2 mole) was added to a solution of potassium permanganate (75 g, 0.47 mole) in water (875 ml) and refluxed till the color of permanganate had discharged. The reaction mixture was filtered hot and the manganese dioxide collected on the filter was washed with hot water (100 ml). After cooling, the combined filtrates were acidified and extracted with ether. The ether extract was washed with water, dried over anhydrous sodium sulphate and evaporated to leave a white solid. Recrystallization from methanol gave 2-(5-phenyl-1,3,4-oxadiazole-2-yl) benzoic acid, M.P. 173°–5°, 3.8 g (7.1%). The infra-red spectrum was identical to that of 2-(5-phenyl-1,3,4-oxadiazole-2-yl) benzoic acid prepared by Method Ia.

EXAMPLE 9. Method IIIb

2-[5-(4-Anisyl)-1,3,4-oxadiazole-2-yl] benzoic acid

The same procedure is used as that for the preparation of 2-(5-phenyl-1,3,4-oxadiazole-2-yl) benzoic acid, Example 7, Method IIIb. The quantities of reagents used differ and p-anisoyl chloride was used in place of benzoyl chloride.
Pyridine (60 ml)
p-Anisoyl chloride (6.9 g, 0.04 mole)
Methyl 2-(5-2H-tetrazolyl) benzoate (4 g, 0.02 mole)
Sodium hydroxide (2 g) in methanol (100 ml)
2-[5-(4-Anisyl)-1,3,4-oxadiazole-3-yl] benzoic acid, M.P. 213°–4° (50% aq. methanol), wt., 3 g (51%).

EXAMPLE 10. Method IIIb

2-[5-(3,5-Dimethylphenyl)-1,3,4-oxadiazole-2-yl] benzoic acid c.f. Example 7, Method IIIb
Methyl 2-(5-2H-tetrazolyl) benzoate (4 g, 0.02 mole)
Pyridine (60 ml)
Sodium hydroxide (2 g) in methanol (100 ml)
3,5-Dimethylbenzoyl chloride (6.5 g, 0.04 mole)
2-[5-(3,5-Dimethylphenyl)-1,3,4-oxadiazole-2-yl] benzoic acid, M.P. 162°–4° (benzene), wt., 2.8 g (48%).

EXAMPLE 11. Method IIIa

Methyl 2-[3,5-dichloro-4-anisyl)-1,3,4-oxadiazole-2-yl] benzoate c.f. Example 5
Methyl 2-(5-2H-tetrazolyl) benzoate (3.75 g, 0.018 mole)
Pyridine (60 ml)
3,5-Dichloro-4-anisoyl chloride (9 g, 0.036 mole)
Methyl 2-[5-(3,5-dichloro-4-anisyl)-1,3,4-oxadiazole-2-yl] benzoate, M.P. 153°–7° (ethanol), wt., 5 g (57%).

EXAMPLE 12. Method IIIa

Methyl 2-[5-[4-methyl-2-(3-pyridyl)-5-thiazolyl-]1,3,4-oxadiazole-2-yl] benzoate c.f. Example 5, Step 4.
The precipitated solid was washed with water and aqueous bicarbonate solution.
Methyl 2-(5-2H-tetrazolyl) benzoate (4 g, 0.04 mole).
Pyridine (60 ml)
4-Methyl-2-(3-pyridyl)-5-thiazolylcarbonyl chloride hydrochloride (9.7 g, 0.04 mole)
Methyl 2-[5-[4-methyl-2-(3-pyridyl)-5-thiazolyl]-1,3,4-oxadiazole-2-yl] benzoate, M.P. 152°–3° (ethanol), wt., 1.8 g (24%).

EXAMPLE 13. Method IIIb

2-[5-(2,4-Dichlorophenyl)-1,3,4-oxadiazole-2-yl] benzoic acid c.f. Example 7, Method IIIb
Methyl 2-(5-2H-tetrazolyl) benzoate (10.5 g, 0.051 mole) Pyridine (150 ml)
2,4-Dichlorobenzoyl chloride (21.0 g, 0.1 mole)
Sodium hydroxide (3 g) in methanol (200 ml)
2-[5-(2,4-Dichlorophenyl)-1,3,4-oxadiazole-2-yl] benzoic acid, M.P. 168°–171°, wt., 5.5 g (31%)

EXAMPLE 14. Method IIIa

Methyl 2-(5-methyl-1,3,4-oxadiazole-2-yl) benzoate

Methyl 2-(5-2H-tetrazolyl) benzoate (16.5 g, 0.08 mole) and acetyl chloride were refluxed for 4 hours on a steam bath. Excess acetyl chloride was removed and the residue heated on the steam bath till effervescence had ceased. Distillation of the residue under reduced pressure gave methyl 2-(5-methyl-1,3,4-oxadiazole-2-yl) benzoate, b.p. 165°–9°/1 mm 8.5 g (48%), a solid at room temperature, M.P. 67°–8°. (Found, C, 60.72, 60.66; H, 4.06, 4.57; N, 12.72, 12.75, $C_{11}H_{10}N_2O_3$ requires C, 60.54; H, 4.62; N, 12.84)

EXAMPLE 15. Method II

2-[5-(3-Chlorophenyl)-1,3,4-oxadiazole-2-yl] benzoic acid c.f. Example 2
2-(3-Chlorophenyl)-5-(2-tolyl)-1,3,4-oxadiazole (54 g, 0.2 mole)
Potassium permanganate (75 g, 0.47 mole) in water (1 l)
Recovered starting material (27 g)
2-[5-(3-Chlorophenyl)-1,3,4-oxadiazole-2-yl] benzoic acid, M.P. 184°–8°, wt. 1.0 (3.3%).

EXAMPLE 16, Method IA

2-[5-(4-Chlorophenyl)-1,3,4-oxadiazole-2-yl] benzoic acid c.f. Example 1, Method Ia
Sulphur trioxide (50 g, 35 ml) in D.M.F. (100 ml)
1-(4-Chlorobenzoyl)-2-(2-carboxybenzoyl)-hydrazine (45 g, 0.15 mole) in D.M.F. (75 ml)
2-[5-(4-Chlorophenyl)-1,3,4-oxadiazole-2-yl] benzoic acid, M.P. 206°–9° (acetone), wt., 9 g (21%). (Found: C, 59.09, 58.88; H, 3.03, 2.97; N, 8.16, 8.16; Cl, 11.48, 10.94, 11.32, 11.51 $C_{15}H_9ClN_2O_3$ requires, C, 59.91; H, 3.02; N, 9.32; Cl, 11.79)

EXAMPLE 17. Method IA

2-[5-(2-Tolyl)-1,3,4-oxadiazole-2-yl] benzoic acid c.f. Example 1, Method Ia
Sulphur trioxide (250 g, 175 ml) in D.M.F. (500 ml)
1-(2-Carboxybenzoyl)-2-(2-toluoyl)-hydrazine (250 g, 0.9 mole) in D.M.F. (200 ml).
2-[5-(2-Tolyl)-1,3,4-oxadiazole-2-yl] benzoic acid, M.P. 154°–5° (acetone/30–65 ligroin), wt., 33.5 g (14%). (Found: C, 67.72, 67.78; H, 4.72, 4.31; N, 8.71, 8.67. $C_{16}H_{12}N_2O_3$ requires C, 68.56; H, 4.32; N, 10.00)

EXAMPLE 18. Method II

2-[5-(2-Anisyl)-1,3,4-oxadiazole-2-yl] benzoic acid c.f. Example 2
2-Anisyl-5-(2-tolyl)-1,3,4-oxadiazole (26 g, 0.1 mole)
Potassium permanganate (37.5 g, 0.24 mole) in water (450 ml)
Recovered starting material (18 g)
2-[5-(2-Anisyl)-1,3,4-oxadiazole-2-yl] benzoic acid, M.P. 157°–160° (benzene/ethanol) wt., 1.7 g (17.9%). (Found: C, 66.22, 65.42; H, 4.46, 4.46; N, 9.68, 9.97. $C_{16}H_{12}N_2O_4$ requires C, 64.86; H, 4.08; N, 9.46.)

EXAMPLE 19. Method II

2-[5-(3-Pyridyl)-1,3,4-oxadiazole-2-yl] benzoic acid c.f. Example 2
2-(3-Pyridyl)-5-(2-tolyl)-1,3,4-oxadiazole (20 g, 0.09 mole)
Potassium permanganate (32 g, 0.02 mole) in water (375 ml)
Recovered starting material (8.5 g)
2-[5-(3-Pyridyl)-1,3,4-oxadiazole-2-yl] benzoic acid, M.P. 213°–5° (ethanol) wt., 5g (36%). (Found: C, 62.83, 62.71; H, 3.64, 3.47; N, 16.17, 16.05. $C_{14}H_9N_3O_3$ requires, C, 62.92; H, 3.39; N, 15.73.)

EXAMPLE 20 METHOD Id

Ethyl 2-(5-phenyl-1,3,4-oxadiazole-2-yl) benzoate 2-(5-Phenyl-1,3,4-oxadiazole-2-yl) benzoic acid (26.6 g, 0.1 mole) in chloroform (100 ml) and thionyl chloride (20 ml) were refluxed for 1 hour. The excess thionyl chloride and chloroform were removed under reduced pressure to leave a colorless oil which slowly solidified. Benzene (100 ml) was added. The resulting solution was added dropwise to a stirred solution of ethanol (6 ml, 0.11 mole) and pyridine (10 ml) in benzene (200 ml). After 12 hours, an equal volume of ether was added. The solution was washed with water (500 ml) N/50 HCl (500 ml), 5% aq. bicarbonate (500 ml) and again with water (500 ml). Evaporation of the ether left a light yellow viscous oil which could not be distilled 23 g (78%).

EXAMPLE 21

Methyl 2-(5-phenyl-1,3,4-oxadiazole-2-yl benzoate 2-(5-Phenyl-1,3,4-oxadiazole-2-yl) benzoic acid (15 g, 0.056 mole) in dry ether (700 ml) was treated with ethereal diazomethane till the color of the ethereal diazomethane persisted. Subsequent filtration and evaporation of the ether left a light yellow oil which could not be distilled. After prolonged refrigeration, a solid was obtained from toluene/ligroin. This gave methyl 2-(5-phenyl-1,3,4-oxadiazole-2-yl) benzoate, M.P. 40°–41°, wt. 8.5 g (54%). (Found: C, 69.39, 69.28; H, 4.47, 4.40; N, 9.33, 9.35. $C_{16}H_{12}N_2O_3$ requires C, 68.56; H, 4.32; N, 10.00.)

EXAMPLE 22

Propargyl 2-(5-phenyl-1,3,4-oxadiazole-2-yl) benzoate 2-(5-Phenyl-1,3,4-oxadiazole-2-yl) benzoic acid (26.6 g, 0.1 mole) was added to a solution of potassium hydroxide (6 g, 0.11 mole) in methanol (250 ml). When all the acid had dissolved, propargyl bromide (20 ml) was added and the reaction mixture refluxed for 2½ hours. The solvent was removed, the residue was dissolved in ether which was subsequently washed with water, aqueous bicarbonate, again with water and dried. Removal of the ether gave a light brown solid which was recrystallised from ether. This gave propargyl 2-(5-phenyl-1,3,4-oxadiazole-2-yl) benzoate as tan-colored crystals, M.P. 99°–101°, 11.5 g (38%). (Found: C, 71.43; H, 4.04; N, 9.27. $C_{18}H_{12}N_2O_3$ requires, C, 71.04; H, 3.98; N, 9.21.)

EXAMPLE 23

Methyl 2-[5-(3-nitrophenyl)-1,3,4-oxadiazole-2-yl] benzoate c.f. Example 22
2-[5-(3-Nitrophenyl)-1,3,4-oxadiazole-2-yl] benzoic acid (31.1 g, 0.1 mole)
Potassium hydroxide (5.6 g, 0.1 mole) in methanol (600 ml)
Methyl iodide (17 ml)
Methyl 2-[5-(3-nitrophenyl)-1,3,4-oxadiazole-2-yl)] benzoate, M.P. 132°–4° (methanol), wt. 33.5 g (97%). (Found: C, 59.39, 58.72; H, 3.52, 3.34; N, 13.15, 12.91. $C_{16}H_{11}N_3O_5$ requires C, 57.51; H, 3.54; N, 13.42.)

EXAMPLE 24

2,3-Epoxypropyl 2-(5-phenyl-1,3,4-oxadiazole-2-yl) benzoate c.f. Example 22, same quantitites, epibromohydrin (15 ml) as alkylating agent. The product, 2,3-epoxypropyl 2-(5-phenyl-1,3,4-oxadiazole-2-yl) benzoate was a viscous oil which could not be distilled, wt. 12 g (37%).

EXAMPLE 25

Butyl 2-(5-phenyl-1,3,4-oxadiazole-2-yl) benzoate c.f. 520, same molar quantities, n-butanol (7.4 g, 9.2 ml, 0.1 mole) used. The product, butyl 2-($SO_3$-phenyl-1,3,4-oxadiazole-2-yl) benzoate was a viscous oil, wt. 25 g (83%).

EXAMPLE 26

Octyl 2-(5-phenyl-1,3,4-oxadiazole-2-yl) benzoate c.f. Example 20, n-octanol (12.5 g, 0.1 mole) used. The product, n-octyl 2-(5-phenyl-1,3,4-oxadiazole-2-yl) benzoate was a viscous oil, wt. 28 g (74%).

EXAMPLE 27

Docecyl 2-(5-phenyl-1,3,4-oxadiazole-2-yl) benzoate c.f. Example 20
Dodecyl alcohol (18.6 g, 0.1 mole)
Dodecyl 2-(5-phenyl-1,3,4-oxadiazole-2-yl) benzoate, a viscous oil, wt. 35 g (81%).

EXAMPLE 28

3-Butynyl 2-(5-phenyl-1,3,4-oxadiazole-2-yl) benzoate c.f. Example 20
3-Butyne-1-ol (7 g, 0.1 mole)
3-Butynyl 2-(5-phenyl-1,3,4-oxadiazole-2-yl) benzoate, a viscous oil, wt. 12 g (38%).

EXAMPLE 29

Method Vb Methyl 2-(5-phenyl-2-oxazolyl) benzoate 2-(5-Phenyl-2-oxazolyl) benzoic acid (5 g, 0.02 mole) in methanol (50 ml) and conc. sulphuric acid (0.5 ml) was refluxed 16 hours. The methanol was removed and the residue dissolved in chloroform. The chloroform solution was washed with dilute bicarbonate solution, water, then dried and evaporated. Recrystallisation of the residue from ethanol gave methyl 2-(5-phenyl-2-oxazolyl) benzoate, M.P. 77°–9°, wt. 3 g (57%). (Found: C, 73.16, 73.40; H, 4.77, 4.72; N, 4.95, 5.00. $C_{17}H_{13}NO_3$ requires C, 73.11; H, 4.69; N, 5.02.)

EXAMPLE 30

Ethyl 2-(5-phenyl-2-oxazolyl) benzoate c.f. Example 29
2-(Phenyl-2-oxazolyl) benzoic acid (10 g, 0.04 mole)
Ethanol (100 ml) conc. sulphuric acid (10 ml)
reflux time — 20 hours
Ethyl 2-(5-phenyl-2-oxazolyl) benzoate, M.P. 49°–50° (ligroin) wt. 8 g (72%). (Found: C, 73.86; 73.99; H, 5.27, 5.20; N, 4.70, 4.85; requires C, 73.80; H, 5.12; N, 4.78.)

EXAMPLE 31 n-Butyl 2-(5-phenyl-2-oxazolyl benzoate c.f. Example 29
2-(5-Phenyl-2-oxazolyl) benzoic acid (10 g, 0.04 mole)
n-Butanol (100 ml), conc. sulphuric acid (0.5 ml)
Heated on steam bath 20 hrs.
n-Butyl 2-(5-phenyl-2-oxazolyl) benzoate, a viscous light yellow oil, wt. 10.5 g (90%).

EXAMPLE 32

Propargyl 2-[5-(3-nitrophenyl)-1,3,4-oxadiazole-2-yl] benzoate c.f. Example 22
2-[5-(3-Nitrophenyl)-1,3,4-oxadiazole-2-yl] benzoic acid (31.1 g, 0.1 mole)
Potassium hydroxide (6g, 0.11 mole) in methanol (250 ml)
Freshly distilled propargyl bromide (20 g)

Propargyl 2-[5-(3-nitrophenyl)-1,3,4-oxadiazole-2-yl)] benzoate, M.P. 124°–6°, wt. 12 g (34%). (Found: C, 61.87, 61.75; H, 3.43, 3.33; N, 12.64, 12.31; $C_{18}H_{11}N_3O_5$ requires C, 61.90; H, 3.16; N, 12.00.)

EXAMPLE 33

Methyl 2-[5-(2-nitrophenyl)-1,3,4-oxadiazole-2-yl] benzoate.

2-[5-(2-Nitrophenyl)-1,3,4-oxadiazole-2-yl] benzoic acid (31 g, 0.1 mole) in acetone (1 l) was treated with dimethyl sulphate (10 ml) and anhydrous potassium carbonate (15 g) The reaction mixture was refluxed and stirred for 20 hours. After the removal of the solvent, the residue was treated with water, and the undissolved material filtered, washed with water and dried. Recrystallisation from acetone gave methyl 2-[5-(2-nitrophenyl)-1,3,4-oxadiazole-2-yl] benzoate, M.P. 165°–9°, 5 g.

EXAMPLE 34

2-[5-(4-Nitrophenyl)-1,3,4-oxadiazole-2-yl] benzoic acid

Crude reaction product from a repeat run of Example 5 was dissolved in methanol (25 ml) and stirred for 2 hrs. in a solution of sodium hydroxide (0.75 g) in methanol (50 ml) Methanol was then removed and the residue was dissolved in water, extracted with ether to remove unreacted ester and acidified. The precipitate was filtered, washed with water and dried. This gave 2-[5-(4-nitrophenyl)-1,3,4-oxadiazole-2-yl] banzoic acid, M.P. 215°–7°, 0.8 g. 1.6 G of methyl ester was obtained from the ether extract.

EXAMPLE 35

To illustrate effectiveness as preemergence herbicides, 150 mg chemical may be dissolved in 5 ml acetone and optionally 30 mg of conventional emulsifying agent (e.g. isooctyl phenyl polyethoxy ethanol; Triton X-100; nonionic surfactant, condensation product of phenyl having isooctyl side chain with about 9 moles of ethylene oxide; also called alpha-[p-(1,1,3,3,-tetramethylbutyl) phenyl]-omega-hydroxypoly [oxyethylene]). The final volume may be increased to 300 ml with distilled water, making a 500 ppm solution. One hundred and sixty milliliters of a 250 and 125 ppm solution are prepared by diluting 80 and 40 ml of the 500 ppm solution with 80 and 120 ml of distilled water, respectively. The chemicals are applied by drenching 80 ml of the respective solutions on the surface of soil in 6-inch plastic pots which had been planted with the following weeds and crops: common lambsquarters (*Chenopodium album* L.), rough pigweed (*Amaranthus retroflexus* L.) purslane (*Portulaca oleracea* L.), large crabgrass (*Digitaria sanquinalis* (L.) Scop.), barnyardgrass (*Echinochloa crusgalli* (L.) Beauv.), giant foxtail (*Setaria faberii* Herrm.), corn (*Zea mays* L.), cotton (*Gossypium hirsutum* L.), and soybeans (*Glycine max* (L.) Merr.). Two seeds of each crop are planted on the diameter one inch below the soil surface in greenhouse soil (3parts loam and 1 part sand). A mixture of the above mentioned broadleaf weeds is planted on the surface of one-half of the pot, and a mixture of the above mentioned grass weeds is planted on the surface of the remaining half. The weed seeds are then covered with a thin layer of soil. There are two replications per treatment. Eighty milliliters of the 125, 250 and 500 ppm solutions, drenched on the soil surface in a 6-inch pot, is equivalent to 5, 10 and 20 lbs/A. The pots are then subirrigated. The results are recorded 14 days after treatment and are reported in Table I.

The results of this test indicate that the oxazoles and oxadiazoles are effective preemergence herbicides. (The rates of application employed in this dosage response example extend to rates higher than necessary in typical agricultural use, with consequent greater crop injury. Selectivity of the chemicals as herbicides is demonstrated in subsequent examples at lower dosages.)

The results also indicate that the substituents of the benzoic acid must be attached at the two position of the benzoic acid in order to have herbicidal activity. In Table I (Part B) compounds (A), (B), (C), (D), (E) and (F), which have the substituents at other than the two position, are outside the invention and are inactive as herbicides; whereas, the other compounds in the test have the substituents at the two position and are active as herbicides. The dibenzoic acid compound (G) is likewise inactive and is outside the invention.

Table I

The percent weed control and percent of crop injury resulting from a soil drench with certain oxazoles and oxadiazoles.

| Compound | Rate Lb/A | Percent Control Broad-Leaf | Grass | Percent Injury Corn | Cotton | Soybean |
|---|---|---|---|---|---|---|
| (Part A) | | | | | | |
| 2-(5-phenyl-1,3,4-oxadiazole-2-yl)benzoic acid | 5 | 85 | 88 | 20 | 90 | 80 |
| | 10 | 93 | 93 | 0 | 100 | 80 |
| | 20 | 90 | 93 | 40 | 100 | 90 |
| 2-[5-(2-chlorophenyl)-1,3,4-oxadiazole-2-yl] benzoic acid | 5 | 70 | 55 | 0 | 60 | 20 |
| | 10 | 70 | 60 | 20 | 80 | 20 |
| | 20 | 80 | 70 | 20 | 80 | 90 |
| 2-[5-(3-chlorophenyl)-1,3,4-oxadiazole-2-yl] benzoic acid | 5 | 75 | 70 | 0 | 50 | 0 |
| | 10 | 75 | 75 | 20 | 90 | 80 |
| | 20 | 90 | 80 | 40 | 100 | 100 |
| 2-[5-(4-chlorophenyl)-1,3,4-oxadiazole-2-yl] benzoic acid | 5 | 90 | 80 | 0 | 100 | 60 |
| | 10 | 90 | 90 | 0 | 100 | 90 |
| | 20 | 95 | 90 | 40 | 100 | 90 |
| 2-[5-(2-tolyl)1,3,4-oxadiazole-2-yl] benzoic acid | 5 | 90 | 90 | 0 | 80 | 60 |
| | 10 | 90 | 88 | 10 | 100 | 50 |
| | 20 | 90 | 90 | 20 | 100 | 80 |
| 2-[5-(2-anisyl)-1,3,4-oxadiazole-2-yl] benzoic acid | 5 | 50 | 80 | 20 | 80 | 60 |
| | 10 | 60 | 80 | 0 | 60 | 20 |
| | 20 | 75 | 85 | 20 | 100 | 60 |
| 2-[5-(3-nitrophenyl)-1,3,4-oxadiazole-2-yl] benzoic acid | 5 | 45 | 50 | 0 | 0 | 0 |
| | 10 | 55 | 55 | 0 | 0 | 0 |
| | 20 | 50 | 55 | 0 | 0 | 0 |
| 2-[5-(3-pyridyl)-1,3,4-oxadiazole-2-yl] benzoic acid | 5 | 40 | 20 | 0 | 100 | 40 |
| | 10 | 70 | 60 | 0 | 70 | 60 |
| | 20 | 80 | 80 | 0 | 70 | 70 |
| 2-[5-(3,4,5-trimethyl-2-furyl)-1,3,4-oxadiazole-2-yl]benzoic acid | 5 | 20 | 10 | 0 | 60 | 0 |
| | 10 | 30 | 35 | 0 | 60 | 20 |
| | 20 | 30 | 40 | 20 | 100 | 20 |
| 2-(5-phenyl-2-oxazolyl) benzoic acid | 5 | 20 | 75 | 0 | 80 | 20 |
| | 10 | 50 | 85 | 40 | 80 | 40 |
| | 20 | 70 | 95 | 60 | 100 | 100 |
| 3-butynyl 2-(5-phenyl-1,3,4,-oxadiazole-2-yl) benzoate | 10(1) | 100 | 92 | — | — | — |
| (Part B) | | | | | | |
| 2-(4-methyl-5-phenyl-2-oxazolyl) benzoic acid | 20(1) | 90 | 90 | — | — | — |
| 2-(5-phenyl-2-oxazolyl) benzoic acid methyl ester | 10(1) | 95(2) | 97 | — | — | — |
| (A) 3-(5-phenyl-1,3,4-oxadiazole-2-yl)benzoic acid | 20(1) | 0 | 0 | — | — | — |
| (B) 4-(5-phenyl-1,3,4,-oxadiazole-2-yl)benzoic acid | 20(1) | 0 | 0 | — | — | — |
| (C) 4-(5-phenyl-1,3,4-oxadiazole-2-yl) benzoic acid | 10(1) | 0 | 0 | — | — | — |
| (D) 4-(1,3,4-oxadiazole-2-yl) benzoic acid ethyl ester | 10(1) | 0 | 0 | — | — | — |

Table I-continued

The percent weed control and percent of crop injury resulting from a soil drench with certain oxazoles and oxadiazoles.

| Compound | Rate Lb/A | Percent Control Broad-Leaf | Grass | Percent Injury Corn | Cotton | Soybean |
|---|---|---|---|---|---|---|
| (E) ethyl 4-[5-(4-nitro-phenyl)-1,3,4-oxadiazole-2-yl] benzoate | 10(1) | 0 | 0 | — | — | — |
| (F) 4-(1,3,4-oxadiazole-2-yl) benzoic acid | 10(1) | 0 | 0 | — | — | — |
| (G) 2,2'-(1,3,4-oxadiazole-2,5-diyl) dibenzoic acid | 20(1) | 0 | 0 | — | — | — |

(1)The drench was applied at only one rate and no crops were included in the test.
(2)This figure based on only pigweed.

EXAMPLE 36

This procedure shows that the oxazoles and oxadiazoles are effective preemergence herbicides when applied to the soil surface as a surface spray.

To prepare an emulsion for spraying, 2.56 g of chemical may be dissolved in 24 ml benzene optionally with 3% of a conventional surfactant such as Tween 80, polyoxyethylene sorbitan monooleate (condensation product of ethylene oxide [20 moles] with sorbitan monooleate).

The final volume may be adjusted to 80 ml with distilled water. Further dilutions of 20 and 10 ml aliquots to 40 ml may be made with distilled water. The solutions are sprayed with a pendulum sprayer delivering 30 gals/A, making applications of 8, 4 and 2lbs/A with the respective solutions. Two seeds of corn, cotton and soybeans were planted in greenhouse soil in 6-inch plastic pots as described in Example 35. The soil surface is then partitioned into six parts. Each part is planted with one of the following species: Rough pigweed, purslane, common morningglory [*Ipomoea purpurea* (L.) Roth], large crabgrass, barnyardgrass and either quackgrass [*Agropyron repens* (L) Beauv.] or giant foxtail. The weed seeds are then covered with a thin layer of soil. After spraying, the soil in each pot is brought to near field capacity by subirrigation. After the initial subirrigation, the pots are watered from above with a fine mist.

The percent weed control and crop injury are recorded 14 days after treatment. The results are reported in Table II. The conditions of this test are more closely related to the manner in which these chemicals would be used in the field. The results indicate that the oxazoles and oxadiazoles are effective herbicides for the control of broadleaf and grass weed species, and that these compounds can selectively control weeds without severely injuring certain crops.

Table II

The percent weed control and percent of crop injury resulting from a surface spray with certain oxazoles and oxadiazoles.

| Compound | Rate Lb/A | Broadleaf Pigweed | Purslane | Common Morningglory | Barnyardgrass | Grass Crabgrass | Quackgrass | Giant Foxtail | Percent Injury Corn | Cotton | Soybeans |
|---|---|---|---|---|---|---|---|---|---|---|---|
| 2-(5-Phenyl-1,3,4-oxadiazole-2-yl) benzoic acid | 2 | 80 | 90 | 0 | 80 | 50 | 50 | — | 0 | 40 | 0 |
|  | 4 | 80 | 95 | 25 | 80 | 60 | 60 | — | 0 | 80 | 80 |
|  | 8 | 90 | 98 | 50 | 90 | 75 | 75 | — | 0 | 80 | 100 |
| 2-(4-Methyl-5-phenyl-2-oxazolyl) benzoic acid | 2 | 80 | 90 | 0 | 70 | 50 | 60 | — | 0 | 40 | 40 |
|  | 4 | 85 | 90 | 100 | 80 | 60 | 60 | — | 20 | 60 | 60 |
|  | 8 | 90 | 90 | 70 | 85 | 80 | 80 | — | 20 | 60 | 60 |
| Methyl 2-(5-phenyl-1,3,4-oxadiazole-2-yl) benzoate | 2 | 85 | * | 50 | 70 | 60 | — | 70 | 20 | 0 | 20 |
|  | 4 | 90 | * | 50 | 80 | 80 | — | 80 | 20 | 0 | 20 |
|  | 8 | 95 | * | 100 | 90 | 85 | — | 90 | 20 | 0 | 20 |
| Methyl 2-[5-(3-nitrophenyl)-1,3,4-oxadiazole-2-yl] benzoate | 2 | 20 | 90 | 20 | 20 | 0 | 0 | — | 40 | 40 | 40 |
|  | 4 | 20 | 50 | 0 | 0 | 20 | 0 | — | 40 | 40 | 40 |
|  | 8 | 40 | 80 | 20 | 20 | 50 | 0 | — | 40 | 0 | 0 |
| Ethyl 2-(5-phenyl-1,3,4-oxadiazole-2-yl) benzoate | 2 | 90 | * | 0 | 70 | 80 | — | 50 | 0 | 0 | 20 |
|  | 4 | 95 | * | 0 | 90 | 85 | — | 75 | 0 | 100 | 20 |
|  | 8 | 100 | * | 50 | 90 | 90 | — | 95 | 40 | 40 | 40 |
| Propargyl 2-(5-phenyl-1,3,4-oxadiazole-2-yl) benzoate | 2 | 80 | 90 | 0 | 80 | 50 | 50 | — | 0 | 40 | 40 |
|  | 4 | 80 | 100 | 40 | 80 | 60 | 50 | — | 0 | 40 | 40 |
|  | 8 | 90 | 90 | 0 | 90 | 60 | 50 | — | 0 | 40 | 40 |
| Butyl 2-(5-phenyl-1,3,4-oxadiazole-2-yl) benzoate | 2 | 95 | * | 0 | 80 | 80 | — | 60 | 0 | 60 | 20 |
|  | 4 | 100 | * | 20 | 90 | 80 | — | 90 | 0 | 60 | 40 |
|  | 8 | 100 | * | 75 | 95 | 90 | — | 95 | 40 | 80 | 40 |
| Octyl 2-(5-phenyl-1,3,4-oxadiazole-2-yl) benzoate | 2 | 80 | * | 0 | 50 | 70 | — | 50 | 0 | 0 | 0 |
|  | 4 | 80 | * | 50 | 70 | 80 | — | 60 | 0 | 0 | 0 |
|  | 8 | 90 | * | 50 | 85 | 85 | — | 70 | 0 | 40 | 0 |
| Dodecyl 2-(5-phenyl-1,3,4-oxadiazole-2-yl) benzoate | 2 | 60 | * | 100 | 20 | 20 | — | 0 | 0 | 40 | 0 |
|  | 4 | 80 | * | 50 | 50 | 50 | — | 20 | 0 | 40 | 0 |
|  | 8 | 85 | * | 50 | 50 | 50 | — | 50 | 0 | 40 | 0 |

*Purslane could not be evaluated in this test because of damping off.

EXAMPLE 37

This procedure shows that the oxadiazoles are effective against purple nutsedge (*Cyperus rotundus* L.).

The chemicals are prepared for treatment by mixing 0.018 g chemical with 50 g fine sand, using a mortar and pestle. The sand and chemical are then transferred to a wide-mouth jar and blended for 15 minutes in a rotary seed mixer. The sand and chemical mixture is then mixed with 400 g greenhouse soil by tumbling in a soil mixer. The soil is then equally divided between three 2.5 inch pots. One purple nutsedge nutlet is planted one inch deep in each pot. The pots are subirrigated. The percent control is determined fourteen days after emergence. The results are reported in Table III.

Table III

The percent control of purple nutsedge resulting from the soil incorporation of certain oxadiazoles.

| Compound | Percent Control Average of Three Replications |
| --- | --- |
| 2-[5-(2-tolyl)-1,3,4-oxadiazole-2-yl] benzoic acid | 88 |
| 2-[5-(4-chlorophenyl)-1,3,4-oxadiazole-2-yl] benzoic acid | 78 |
| 2-[5-(2-chlorophenyl)-1,3,4-oxadiazole-2-yl] benzoic acid | 80 |
| 2-[5-(3-pyridyl)-1,3,4-oxadiazole-2-yl] benzoic acid | 90 |

The foregoing data indicate that the oxadiazoles can effectively control purple nutsedge. Purple nutsedge, a member of the Cyperaceae family, is considered to be the worst weed in the world. There are not many herbicides which effectively control the members of the Cyperaceae selectively. Therefore, the ability of the oxadiazoles to control purple nutsedge is a significant discovery.

EXAMPLE 38

This example will further substantiate the effectiveness of the oxadiazoles in controlling members of the Cyperaceae selectively. The compound, 2-(5-phenyl-1,3,4-oxadiazole-2-yl) benzoic acid, is formulated as a 3 lb/gal ammonium salt. The formulated chemical is applied at 4, 8 and 16 lbs/A to an established cranberry (*Vaccinium macrocarpon* Ait.) bog in early spring. At the time the cranberry plants are dormant, and the weeds have not yet emerged. The plot size is 8×8 feet and is replicated four times. Weed control and crop injury data are taken in the following early fall.

The major weed in the bog was nutgrass (*Cyperus dentatus* Torr.), a member of the Cyperaceae family. At all three rates weed control was 100% and there was no crop injury. This activity of the oxadiazoles is particularly unique in that it results in the control of a weed which is difficult to control in a crop on which few herbicides can be used.

EXAMPLE 39

This example will show that certain oxazoles and oxadiazoles are also active as postemergence herbicides.

A 6000 ppm sodium salt solution of the chemical to be sprayed may be prepared by dissolving 0.6 g of the chemical and a stoichiometric amount of 5% sodium bicarbonate in 10 ml acetone (and optionally 30 mg isooctylphenylpolyethoxyethanol) and then diluting to 100 ml. One purple nutsedge nutlet is planted in the center of a 4.5 inch pot. The following weeds are planted as described in Example 35: purslane, rough pigweed, common moringglory, large crabgrass, barnyardgrass, and giant foxtail. The plants are maintained in a 16 hour photoperiod. The plants are sprayed when the broadleaf weeds are 1.5 inches tall and the grass weeds are 1 to 3 inches tall. The plants are sprayed to runoff with a De Vilbiss No. 152 sprayer from a distance of 18 inches for 20 seconds at 20 psi. There are two replications. The pots are subirrigated. The percent weed control is determined five days after treatment. The results are reported in Table IV.

The results indicate that the oxazoles and oxadiazoles are effective in controlling weeds when applied as a postemergence herbicide.

Table IV

The percent weed control resulting from a postemergence spray with certain oxazoles and oxadiazoles at 6000 ppm.

| | Percent Weed Control | | | | | | |
| --- | --- | --- | --- | --- | --- | --- | --- |
| Compound | Purs-lane | Pig-weed | Common Morning-glory | Crab-grass | Giant Foxtail | Barn-yard-grass | Purple Nuts-edge |
| 2-(5-phenyl-1,3,4-oxadiazole-2-yl) benzoic acid | 50 | 80 | 60 | 50 | 50 | 50 | 25 |
| 2-[5-(2-tolyl)-1,3,4-oxadiazole-2-yl] benzoic acid | 75 | 90 | 75 | 70 | 60 | 60 | 25 |
| 2-[5-(4-chlorophenyl)-1,3,4-oxadiazole-2-yl] benzoic acid | 50 | 80 | 60 | 50 | 50 | 50 | 25 |
| 2-[5-(3-nitrophenyl)-1,3,4-oxadiazole-2-yl] benzoic acid | 20 | 75 | 50 | 50 | 50 | 50 | 0 |
| 2-[5-(3-pyridyl)-1,3,4-oxadiazole-2-yl] benzoic acid | 0 | 75 | 25 | 50 | 50 | 50 | 25 |
| 2-(5-phenyl-2-oxazolyl) benzoic acid | 80 | 90 | 50 | 60 | 50 | 30 | * |
| 2-(4-methyl-5-phenyl-2-oxazolyl) benzoic acid | 80 | 90 | 75 | 60 | 50 | 50 | * |

*Purple nutsedge not included in the test.

EXAMPLE 40

Example 35 is repeated, using chemicals as shown in Table V, with the results listed in said Table.

Table V

The percent weed control resulting from a soil drench with certain oxazoles and oxadiazoles

| Chemical | Lb/A | Pigweed | Purslane | Common Morning-glory | Barnyardgrass | Crabgrass | Giant Foxtail | Purple Nutsedge |
|---|---|---|---|---|---|---|---|---|
| 2,3-epoxypropyl 2-(5-phenyl-1,3,4-oxadiazole-2-yl) benzoate | 10 | 50 | 80 | 0 | 80 | 70 | 50 | |
| methyl 2-[5-(2-nitrophenyl)-1,3,4-oxadiazole-2-yl] benzoate | 10 | 25 | 80 | 0 | 95 | 90 | 70 | 100 |
| | 20 | 80 | 50 | 0 | 100 | 80 | 90 | 100 |
| 2-[5-(2,5-dichlorophenyl)-1,3,4-oxadiazole-2-yl] benzoic acid | 10 | 100 | 90 | 30 | 80 | 50 | 50 | 0 |
| methyl 2-[5-(4-nitrophenyl)-1,3,4-oxadiazole-2-yl] benzoate | 10 | 80 | 60 | 0 | 0 | 60 | 40 | 0 |
| | 20 | 90 | 80 | 20 | 50 | 80 | 50 | 0 |
| propargyl 2-[5-(3-nitrophenyl)-1,3,4-oxadiazole-2-yl] benzoate | 10 | 50 | 40 | 0 | 0 | 50 | — | 0 |
| methyl 2-[5-(3,5-dichloro-4-anisyl)-1,3,4-oxadiazole-2-yl] benzoate | 10 | 50 | 60 | 0 | 50 | 60 | — | 0 |
| 2-[5-(4-nitrophenyl)-1,3,4-oxadiazole-2-yl] benzoic acid | 10 | 90 | 90 | 50 | 90 | 90 | — | 0 |
| 2-[5-(5-anisyl)-1,3,4-oxadiazole-2-yl] benzoic acid | 10 | 80 | 60 | 50 | 70 | 60 | — | 0 |
| n-butyl 2-(5-phenyl-2-oxazolyl)benzoate | 10 | 90 | 90 | 50 | 60 | 50 | — | 0 |
| ethyl 2-(5-phenyl-2-oxazolyl) benzoate | 10 | 60 | 60 | 0 | 60 | 40 | — | 0 |
| methyl 2-(5-methyl-1,3,4-oxadiazole-2-yl) benzoate | 5 | 50 | 95 | 0 | 0 | 0 | — | 0 |
| | 10 | 80 | 95 | 50 | 40 | 50 | — | 0 |
| 2-[5-(3,5-dimethylphenyl)-1,3,4-oxadiazole-2-yl]benzoic acid | 5 | 80 | 90 | 75 | 80 | 70 | — | 10 |
| | 10 | 90 | 95 | 100 | 90 | 85 | — | 10 |

Having thus described our invention, what we claim and desire to protect by Letters Patent is:

1. A method of controlling weeds which comprises applying to a locus containing weed seeds or supporting weed growth a herbicidally effective amount of a chemical having the structural formula

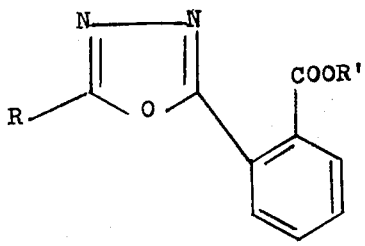

wherein R is selected from the group consisting of phenyl, phenyl substituted with up to three substituents wherein the substituents are halo, nitro, alkyl having up to 4 carbon atoms or alkoxy having up to 4 carbon atoms, 4-methyl-2-(3-pyridyl)-5-thiazolyl, alkyl having up to 6 carbon atoms, and 3-pyridyl;

and R' is hydrogen, alkali metal, ammonium, or a moiety having up to 12 carbon atoms selected from alkyl, alkynyl and epoxyalkyl.

2. A method as in claim 1 in which R is phenyl.
3. A method as in claim 1 in which R' is hydrogen.
4. A method as in claim 1 in which R' is alkyl.
5. The method of claim 1 in which R is phenyl and R' is hydrogen.
6. The method of claim 1 in which R is phenyl and R' is n-butyl.

* * * * *